US011453006B2

(12) United States Patent
Liu

(10) Patent No.: US 11,453,006 B2
(45) Date of Patent: Sep. 27, 2022

(54) CHIP FOR SEPARATING AND CAPTURING CELL AND APPLICATION OF CHIP IN TUMOR CELL SORTING THEREOF

(71) Applicant: ZIGZAG BIOTECHNOLOGY CO., LTD., Shenzhen (CN)

(72) Inventor: Zongbin Liu, Shenzhen (CN)

(73) Assignee: ZIGZAG BIOTECHNOLOGY CO., LTD., Shenzhen (CN)

( * ) Notice: Subject to any disclaimer, the term of this patent is extended or adjusted under 35 U.S.C. 154(b) by 442 days.

(21) Appl. No.: 16/643,703

(22) PCT Filed: Apr. 4, 2018

(86) PCT No.: PCT/CN2018/081930
§ 371 (c)(1),
(2) Date: Mar. 2, 2020

(87) PCT Pub. No.: WO2019/085388
PCT Pub. Date: May 9, 2019

(65) Prior Publication Data
US 2020/0238286 A1     Jul. 30, 2020

(30) Foreign Application Priority Data

Nov. 1, 2017  (CN) .......................... 201711055249.2

(51) Int. Cl.
B01L 3/00      (2006.01)
(52) U.S. Cl.
CPC ... B01L 3/502753 (2013.01); B01L 3/502761 (2013.01); *B01L 2200/0652* (2013.01);
(Continued)

(58) Field of Classification Search
CPC ......... B01L 2200/0652; B01L 2200/16; B01L 2300/06; B01L 2300/0819;
(Continued)

(56) References Cited

FOREIGN PATENT DOCUMENTS

| CN | 105062866 A | * 11/2015 |
| CN | 105062866 A |   11/2015 |

(Continued)

OTHER PUBLICATIONS

China Patent Office "International Search Report" dated Jul. 31, 2018, China.

*Primary Examiner* — Jennifer Wecker
(74) *Attorney, Agent, or Firm* — WPAT, PC

(57) ABSTRACT

The present disclosure relates to an integrated chip, which includes a cell enrichment region, a cell separation region and a cell capture region, wherein one end of the cell enrichment region is provided with an inlet, and the other end of the cell enrichment region is provided with a waste liquid outlet and an enriched liquid outlet; one end of the cell separation region is provided with a buffer solution inlet and an enriched liquid inlet , and the other end of the cell separation region is provided with an outlet; one end of the cell capture region is provided with an inlet, and the other end of the cell capture region is provided with a separated liquid outlet. Compared with the traditional technology, the chip can separate a target cell from a to-be-treated cell solution with a high efficiency, and capture the target cell in situ in a chip.

20 Claims, 13 Drawing Sheets

(52) U.S. Cl.
CPC ....... *B01L 2200/16* (2013.01); *B01L 2300/06* (2013.01); *B01L 2300/0819* (2013.01); *B01L 2300/0867* (2013.01); *B01L 2300/12* (2013.01)

(58) Field of Classification Search
CPC ..... B01L 2300/0864; B01L 2300/0867; B01L 2300/12; B01L 2400/086; B01L 3/502753; B01L 3/502761; C12M 47/04; C12N 2509/00; C12N 5/0693
See application file for complete search history.

(56) References Cited

FOREIGN PATENT DOCUMENTS

| | | | | |
|---|---|---|---|---|
| CN | 106754344 A | 5/2017 | | |
| WO | WO-2014145075 A2 * | 9/2014 | ............. | A61K 35/14 |
| WO | WO-2018080997 A1 * | 5/2018 | ............. | A61K 35/17 |

* cited by examiner

Unit: μm

Unit: μm

Unit: μm

CHIP FOR SEPARATING AND CAPTURING CELL AND APPLICATION OF CHIP IN TUMOR CELL SORTING THEREOF

CROSS REFERNCE TO RELATED APPLICATIONS

This application is the national phase entry of International Application No. PCT/CN2018/081930, filed on Apr. 4, 2018, the entire contents of which are incorporated herein by reference.

FIELD OF TECHNOLOGY

The present disclosure relates to the technical field of biology, in particular to a method for sorting cells, and specifically in particular to an integrated chip for separating and capturing cells with one step and an application in aspect of tumor cell sorting thereof.

BACKGROUND OF THE INVENTION

Circulating Tumor Cells (CTCs) are tumor cells which shed from a primary lesion or a metastasis lesion of a tumor and enter blood through a blood vessel or a lymphatic system. The CTCs from the primary or metastasis lesion can not only indirectly embody a characteristic of the tumor, but also reflect a development status of the tumor. Compared with a traditional tumor screening diagnostic method (an oncoradiology, a serum tumor marker and a tissue biopsy), the detection of the CTCs has a unique and important clinical application value.

1. The oncoradiology is a conventional tumor screening method. However, for a relatively small tumor lesion (smaller than 1 cm), due to a volume effect, missed diagnosis occurs easily. However, it is found by researchers that even if a tumor tissue is small (such as 2-4 mm), the tumor cells may also shed into the blood. In this sense, the detection of the CTCs may serve as an auxiliary method for early diagnosis of the tumor.

2. The examination of the serum tumor marker is also the conventional clinical screening method. Nevertheless, the blood of a healthy person also has a certain level of markers; and due to individual and physiological differences of a patient, a false positive and a false negative occur easily, and the specificity is not high enough. On the contrary, the detection of the CTCs has a high specificity and the blood of the healthy persons does not have the CTCs.

3. The tissue biopsy is a conventional diagnostic analysis method but is also the invasive examination and has a potential risk of cancer cell metastasis. Conversely, the detection of the CTCs is considered as a non-invasive and repeatable novel liquid biopsy technique with a low cost. The liquid biopsy technique based on the CTCs may not only dynamically monitor and determine prognosis (the number of CTCs), but also be used for guiding treatment (a biological characteristic of the CTCs).

Since the number of CTCs in peripheral blood is small and there are only several tumor cells in one hundred million of leukocytes and erythrocytes, the separation and capture of the CTCs are a foundation for subsequent analysis (a phenotype and a genotype). Presently, methods for separating the CTCs are mainly classified as per a principle to be based on biological and physical characteristics of the cells.

1. Separation Based on Biological Characteristics of Tumor Cells

The CTCs are a kind of epithelial cells, and can express a specific antigen of the epithelial cells, such as an Epithelial Cell Adhesion Molecule (EpCAM). An antibody of the EpCAM may be used for separating and capturing the CTCs. The most typical method is a CellSearch system developed by Johnson & Johnson Company in U.S. With the utilization of the EpCAM to combine with a magnetic bead including a specific antibody, the tumor cells may be separated out under the action of an external magnetic field. The CellSearch is a CTCs separation and capture platform solely approved by U.S. Food and Drug Administration (FDA) in clinical use. However, the researches show that the specific antigen EpCAM of the epithelial cells is down-regulated in expression after the spreading of the cancer cells to the blood, and the tumor cells with the down-regulated expression cannot be captured. In order to overcome the defect, separation methods based on the physical characteristics of the cells are developed by researchers.

2. Separation Based on Physical Characteristics of Tumor Cells

The physical characteristics of the tumor cells, such as size and density, are greatly different from those of the leukocytes and the erythrocytes. For example, diameters of the tumor cells are generally greater than 12 μm, and diameters of the leukocytes are mostly smaller than 15 μm. By virtue of this difference, the tumor cells may be separated from the blood. Common separation methods based cell sizes are, for example, filter membranes, inertia force, vortex, Deterministic Lateral Displacement (DLD), etc.

The present disclosure uses CTCs separation based on a DLD principle. The DLD principle is to firstly design micropost arrays arranged as per a certain direction. According to sizes and arrangements of the micropost arrays, each micropost array has a specific substance critical sorting size (diameter). A large substance greater than the critical diameter has a lateral displacement after being collided with the micropost array and is gathered to one side, and a substance smaller than the critical diameter does not have the lateral displacement after being collided with the array and keeps an original flow direction. As a result, the large substance and the small substance are spatially separated.

The sizes of the tumor cells are often greater than those of the leukocytes and the erythrocytes. There have been some reports that the CTCs in the peripheral blood are separated by using the DLD arrays. In the traditional technology, a symmetrical triangular-micropost DLD chip structure is designed. The blood is perfused into the chip via a chip inlet. Relatively large cells (above the critical size of 6-8 μm) including the tumor cells and a part of leukocytes are finally enriched to a middle of a flow channel to be collected. However, the erythrocytes and the leukocytes located in the middle portion of the flow channel cannot be separated, so that the separation purify of the tumor cells is very low (lower than 0.01%).

In traditional technology, a similar symmetrical triangular-micropost chip structure is further designed. A buffer solution inlet is designed in the middle of the flow channel The erythrocytes are removed completely, and the tumor cells and a part of leukocytes (above the critical size of 6.5-8.5 μm) are enriched to the buffer solution in the middle of the flow channel to be collected. Nevertheless, a great number of leukocytes greater than the critical size still exist in the blood, so the separated liquid has a low purity of tumor cells and a high concentration of leukocytes, and needs to be purified secondarily. Additionally, the DLD chips reported in the art has a narrow width (3-5 mm). In order to improve the separation throughput, a relatively high flow velocity is required, which results in that the cells are damaged, and the subsequent staining and biological analysis of the tumor cells are affected.

The defects of the traditional technology lie in: firstly, the high-purity CTCs cannot be separated; and secondly, after the separation with the DLD chip, the CTCs are subjected to centrifugation, resuspension and other operations, and collected to a pore plate, a culture vessel or a chip for staining and identification. The multi-step operation will cause loss and damage of the cells, so it is necessary to decrease operation steps after the separation or integrate these operations into one process. However, there hasn't been a relevant report till now.

SUMMARY

The present disclosure provides an integrated chip for separating and capturing a cell with one step and a use method and an application thereof, which can separate cells with high efficiency, high purity and high activity, and capture cells in situ in the chip.

One objective of the present disclosure is to provide an integrated chip for separating and/or capturing cells with one step.

The integrated chip for separating and/or capturing cells provided by the present disclosure may be the following (A) or (B) or (C) or (D).

(A) An integrated chip for separating cells with one step includes but not limited to a cell separation region; one end of cell separation region with a cell solution inlet and a buffer solution inlet, and the other end of the cell separation region is provided with an outlet; a to-be-separated cell solution passing through the cell solution inlet, and a buffer solution passing through the buffer solution inlet jointly flow into the cell separation region; and the cell separation region is capable of separating the inflowed cell as per a size.

(B) An integrated chip for separating and capturing cells with one step includes but not limited to a cell separation region and a cell capture region; one end of the cell separation region is provided with a cell solution inlet and a buffer solution inlet, and the other end of the cell separation region is provided with an outlet; one end of the cell capture region is provided with an inlet connecting with the outlet of the cell separation region, and the other end of the cell capture region is provided with a separated liquid outlet; a to-be-separated cell solution passing through the cell solution inlet, and a buffer solution passing through the buffer solution inlet jointly flow into the cell separation region; the cell separation region is capable of separating the inflowed cell as per a size; cells separated as per the size enters the cell capture region; and the cell capture region can capture target cells.

(C) An integrated chip for separating cells with one step includes but not limited to a cell enrichment region and a cell separation region; one end of the cell enrichment region is provided with one or more inlets, and the other end of the cell enrichment region is provided with a waste liquid outlet and an enriched liquid outlet; one end of the cell separation region is provided with a buffer solution inlet and an enriched liquid inlet connecting with the enriched liquid outlet of the cell enrichment region, and the other end of the cell separation region is provided with an outlet; a to-be-separated cell solution is perfused from the inlet of the cell enrichment region to enter the cell enrichment region; the cell enrichment region is capable of improving a concentration of target cells in the cell solution, so as to facilitate subsequent further separation; a waste liquid flows out from the waste liquid outlet; an enriched liquid flowing out from the cell enrichment region and passing through the enriched liquid inlet, and a buffer solution passing through the buffer solution inlet jointly flow into the cell separation region; and the cell separation region is capable of separating the inflowed cell as per a size.

(D) An integrated chip for separating and capturing cells with one step includes but not limited to a cell enrichment region, a cell separation region and a cell capture region; one end of the cell enrichment region is provided with one or more inlets, and the other end of the cell enrichment region is provided with a waste liquid outlet and an enriched liquid outlet; one end of the cell separation region is provided with a buffer solution inlet and an enriched liquid inlet connecting with the enriched liquid outlet of the cell enrichment region, and the other end of the cell separation region is provided with an outlet; one end of the cell capture region is provided with an inlet communicating with the outlet of the cell separation region, and the other end of the cell capture region is provided with a separated liquid outlet; a to-be-separated cell sap is charged from the inlet of the cell enrichment region to enter the cell enrichment region; the cell enrichment region is capable of improving concentration of target cells in the cell solution, so as to facilitate subsequent further separation; a waste liquid flows out from the waste liquid outlet; an enriched liquid flowing out from the cell enrichment region and passing through the enriched liquid inlet, and a buffer solution passing through the buffer solution inlet jointly flow into the cell separation region; the cell separation region is capable of separating the inflowed cell as per a size; the cell separated as per the size enters the cell capture region; and the cell capture region is capable of capturing the target cell.

Further, multiple inlets provided on one end of the cell enrichment region includes but not limited to the cell solution inlet and/or the buffer solution inlet.

Further, the cell enrichment region is composed of one, two or more sets (such as three sets) of symmetrical Deterministic Lateral Displacement (DLD) micropost array structures; cells greater than a critical sorting diameter of the symmetrical DLD microcolumn array structure are enriched to a middle of the symmetrical DLD microcolumn array structure when flowing through the cell enrichment region, gathers and then flows into the cell separation region; and the waste liquid flows out from the waste liquid outlet.

Further, when the cell enrichment region is composed of two and more sets of symmetrical DLD array structures, two sets of adjacent symmetrical DLD array structures are separated by a column.

Further, a DLD micropost of the cell enrichment region is one of a triangular structure, a circular structure, a rectangular structure, an "H-shaped structure and a special-shaped structure.

Further, in the cell enrichment region, the critical sorting diameter of the symmetrical DLD micropost array structure is 1-30 µm. Preferably, the critical sorting diameter is 3-15 µm. More preferably, the critical sorting diameter is 5-10 µm.

In an embodiment of the present disclosure, the critical sorting diameter of the symmetrical DLD microcolumn array structure is 6-8 µm specifically.

Further, in the cell enrichment region, the DLD micropost in the symmetrical DLD micropost array structure converges to an axis of symmetry as per an inclination angle of 0.1-30°. Preferably, the inclination angle is 1-20°.

In an embodiment of the present disclosure, the inclination angle of the DLD micropost in the symmetrical DLD micropost array structure is 1.2° specifically.

Further, the DLD microarray of the cell enrichment region is the triangular structure, one vertex of the triangle points to the axis of symmetry of the symmetrical DLD micropost array structure where the vertex is located, an edge of the triangle is 1-500 μm long, and a gap between two adjacent triangles is 1-500 μm. Preferably, the edge is 10-50 μm long, and the gap between two adjacent triangles is 10-50 μm. More preferably, the edge is 15-40 μm long, and the gap between two adjacent triangles is 15-50 μm. The "gap between two adjacent triangles" refers to a longitudinal row gap or a transverse micropost gap.

In an embodiment of the present disclosure, the DLD micropost of the cell enrichment region is the triangular structure, the edge of the triangle is 20 μm long specifically, and the gap between two adjacent triangles is 25 μm (row gap) and 50 μm (micropost gap).

Further, the cell separation region is composed of the DLD micropost array structure; a DLD micropost of the cell separation region is one of a triangular structure, a circular structure, a rectangular structure, an "H-shaped structure and a special-shaped structure; and the DLD micropost array structure of the cell separation region has a gradually increased critical sorting diameter or an unchanged critical sorting diameter from an inlet side to an outlet side of the cell separation region.

Further, the gradually increased critical sorting diameter is 1-50 μm from the inlet side to the outlet side of the cell separation region, preferably 3-30 μm, and more preferably 5-25 μm.

The gradual increase is a linear increase, a gradient increase or a combination thereof.

In an embodiment of the present disclosure, the gradually increased critical sorting diameter of the DLD micropost array of the cell separation region from the inlet side to the outlet side of the cell separation region is set as follows: from 8 μm on the inlet side to 20 μm on the outlet side in a gradient manner (the gradient is provided every 4 μm).

Further, the unchanged critical sorting diameter is 1-50 μm, preferably 3-30 μm, and more preferably 8-20 μm.

In an embodiment of the present disclosure, the unchanged critical sorting diameter is 15 μm specifically.

Further, the DLD micropost array of the cell separation region has a gradually increased inclination angle from the inlet side to the outlet side of the cell separation region: the inclination angle is gradually increased from 0.1-15° on the inlet side to 0.2-30° on the outlet side, preferably, the inclination angle is gradually increased from 1-5° on the inlet side to 10-25° on the outlet side. Compared with a fixed inclination angle of the DLD micropost array, the inclination angle increased from the inlet side to the outlet side may guarantee that the cells having different sizes are separated gradually, so that the purity and efficiency of cell sorting are improved. A larger inclination angle generates a larger critical separation diameter, so that the cell is spatially arranged as per the size at the outlet of the separation region.

In an embodiment of the present disclosure, the gradually increased inclination angle of the DLD micropost array of the cell separation region from the inlet side to the outlet side of the cell separation region is set as follows: from 1.2° on the inlet side to 10.2° on the outlet side in a gradient manner (the gradient is provided every 3°).

Further, the cell capture region includes a first region and a second region; the first region is composed of a micropost capture structure array, and configured to capture the target cells; a micropost capture structure is a micropost having a large opening inlet and a small outlet; the micropost capture structure in the micropost capture structure array is staggered; the second region is composed of a non-micropost capture structure array; a non-target cell flows out via the second region; a non-micropost capture structure is one of a triangular microcolumn, a circular microcolumn, a rectangular microcolumn, an "H-shaped microcolumn or a special-shaped structural micropost; and the non-micropost capture structure in the non-micropost capture structure array is aligned in a row.

Further, the cell capture region has one or more first regions and second regions.

Further, in the first region, a diameter of the opening of the micropost capture structure is 15-30 μm, and a diameter of the outlet is 3-8 μm; and preferably, the diameter of the opening is 15-20 μm, and the diameter of the outlet is 3-6 μm. In the micropost capture structure array, a vertical gap between every two adjacent microcolumn capture structures is 8-30 μm, preferably 22 μm. In the non-micropost capture structure array, a vertical gap between every two adjacent non-microcolumn capture structures is 8-30 μm, preferably 22 μm. In an embodiment of the present disclosure, the diameter of the opening of the micropost capture structure in the first region is 16 pm specifically, and the diameter of the outlet is 4 μm specifically. In the micropost capture structure array, the vertical gap between every two adjacent microcolumn capture structures is 22 μm specifically. In the non-micropost capture structure array, the vertical gap between every two adjacent microcolumn capture structures is 22 μm specifically.

Further, the integrated chip is made of one or more of glass, silicon and a polymer; and the polymer may be one or more of polymethyl methacrylate, polycarbonate, polystyrene, polyethylene, silicon resin (such as poly(dimethylsiloxane)), polyvinyl acetate, polypropylene, polyvinyl chloride, polyether ether ketone, a polyethylene glycol terephthalate cycloolefin polymer (COP) and a cycloolefin copolymer (COC).

The present disclosure further provides a method for separating and/or capturing a cell with one step.

The method for separating and/or capturing the cell with one step provided by the present disclosure uses the integrated chip provided by the present disclosure to separate and/or capture cells from a to-be-separated cell sap with one step, and includes the following step: flowing the to-be-separated cell solution through a cell separation region of the integrated chip.

Further, the method for separating and/or capturing cells with one step provided by the present disclosure may specifically include the following steps: perfusing the to-be-separated cell solution from an inlet of a cell enrichment region of the integrated chip to enter the cell enrichment region, and subjecting the to-be-separated cell sap to treatment of a symmetrical DLD micropost array structure, where cells greater than a critical sorting diameter are enriched to a middle of the symmetrical DLD microcolumn array structure (a concentration of cells in the cell solution is improved), gathers and then flows into the cell separation region, and a waste liquid flows out from a waste liquid outlet; passing an enriched liquid, flowing out from the cell enrichment region, through an enriched liquid inlet, and passing a buffer solution through a buffer solution inlet, thus jointly flowing into the cell separation region, and sorting by the DLD micropost array structure of the cell separation region, where cells in the enriched liquid are separated as per a size; entering the cell separated as per the size to a cell capture region, where a first region of the cell capture region captures target cells; flowing out non-target cells through a second region, and flowing out a separated liquid from a separated liquid outlet; and directly carrying out staining analysis and/or sequencing research on the target cells captured by the cell capture region.

Further, a volume ratio of the cell solution or the enriched liquid to the buffer solution flowing into the cell separation region is 1:(1-50), preferably 1:(3-30) and more preferably 1:(4-15).

In an embodiment of the present disclosure, the volume ratio of the enriched liquid to the buffer solution flowing into the cell separation region is 1:10 specifically.

In an embodiment of the present invention, a flux of the cell solution perfused to the integrated chip is 5-25 mL/h specifically.

Further, any one of the followings may be perfused to the inlet of the enrichment region: (a) a stoste of the to-be-separated cell solution; (b) a diluent of the to-be-separated cell solution; (c) the stoste and the buffer solution of the to-be-separated cell solution; and (c) the diluent and the buffer solution of the to-be-separated cell solution.

Another objective of the present invention is to provide an application of the integrated chip for separating and/or capturing cells with one step.

The application is an application of the integrated chip in separating and/or capturing cells.

Further, the application includes but not limited to any one of the followings: (1) separating and/or capturing a CTCs in a peripheral blood sample; (2) separating and/or capturing tumor cells in a pleural effusion, peritoneal effusion, lymph fluid, urine or bone marrow sample; (3) separating and/or capturing a nucleated erythrocytes in a peripheral blood or umbilical cord blood sample; (4) separating and/or capturing circulating endothelial cells in the peripheral blood sample; (5) separating and/or capturing leukocytes, T cells, B cells, lymphocytes, monocytes, natural killer cells, dendritic cells, macrophages or a hematopoietic stem cells in a peripheral blood, umbilical cord blood, pleural effusion, peritoneal effusion, urine, cerebrospinal fluid or bone marrow sample; (6) separating and/or capturing erythrocytes or platelets in peripheral blood, umbilical cord blood, pleural effusion, peritoneal effusion, urine or bone marrow sample; (7) separating and/or capturing bacteriums or virus in a peripheral blood, pleural effusion, peritoneal effusion, urine, saliva, plasma, serum, cerebrospinal fluid, seminal fluid, prostatic fluid or vaginal secretion sample; and (8) separating and/or capturing sperms in a seminal fluid sample.

In an embodiment of the present disclosure, the target cells are hepatocellular tumor cells, specifically a HepG2; and the non-target cells are leukocytes and an erythrocytes.

The integrated chip provided by the present disclosure can capture the separated target cells in situ, and directly carry out flow cytometry, sound focusing, nuleic acid or protein analysis, gene sequencing, nuleic acid library construction and cell culture analysis; or analyze with microscopy, including immunofluorescent staining and fluorescence in situ hybridization (FISH) staining The present disclosure has the following advantages: compared with the traditional technology, an integrated chip for separating and capturing cells with one step provided by the present disclosure can separate target cells from a to-be-treated cell solution with a high efficiency, a high purity and a high activity, and capture the target cells in situ in the chip . Specifically, the advantages are as follows:

1. Improvement of Separation Throughput

The improvement of the separation throughput is implemented by a cell enrichment region. In case of only one set of micropost structure, a flow channel is narrow and the throughput cannot be improved effectively. The present disclosure may use two or more sets of symmetrical microcolumn structures to improve the flux by two or more times.

2. Improvement of Separation Purity

The improvement of the separation purity is implemented by a cell separation region. The micropost array structure designed in the traditional technology only has one inclination angle, so that the cell cannot be separated accurately as per a size, only the cells greater than a clinical size can be enriched and the purity of the separated cell cannot be improved. An inclination angle of a triangular microcolumn array in the cell separation region of the present disclosure is gradually increased from 0.1-15° on an inlet side of the separation region to 0.2-30° on an outlet side, and a larger angle generates a larger critical separation diameter, so that the cells are spatially arranged according to the size at the outlet of the separation region; and the purity of CTCs in the cell separation region with the relatively large size is obviously improved.

3. In-Situ Capture of Cell

There hasn't been a report on use of a DLD chip for separation and capture of the cell so far. The present disclosure describes a first method on use of a DLD micropost structure for the separation and capture.

4. Improvement of Viability of Separated Cells

The chip designed in the traditional technology can only implement cell enrichment, and secondary or repeated purification is needed for separation to obtain high-purity cells; however, the multi-step operation leads to loss and damage of the cell. On the contrary, the one-step integrated operation of the present disclosure reduces the human intervention and operation, thus improving the activity of the cell obviously.

5. Reduction of Cost

The integrated operation reduces the use of a manual labor and a consumable, and obviously reduces a detection cost.

BRIEF DESCRIPTION OF THE DRAWINGS

In FIG. 22, FIG. 23 and FIG. 24, a concentration of a cancer cell in a simulated sample is about 100 cancer cells in each milliliter and a flux of a cell solution is about 20 mL/h.

In the figures: 1-cell enrichment region, 2-cell separation region, 3-cell capture region, 4-inlet of enrichment region, 5-waste liquid outlet, and 6-outlet of capture region.

DESCRIPTION OF THE EMBODIMENTS

The following embodiments are used for illustrating the present disclosure rather than limiting the scope of the present disclosure.

Embodiment 1

Figure 1:
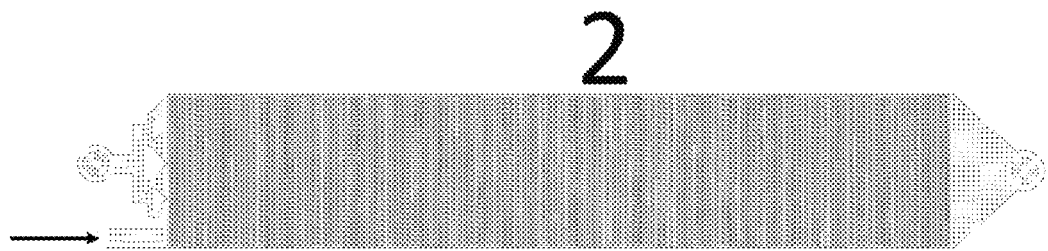
FIG. 1 is an overall structural schematic diagram of an integrated chip for separating and capturing cells with one step in Embodiment 1 of the present disclosure.

As shown in FIG. 1, an integrated chip for separating cells with one step includes a cell separation region 2; one end of the cell separation region 2 is provided with a cell solution inlet and a buffer solution inlet, and the other end of the cell separation region 2 is provided with an outlet; a to-be-separated cell solution passing through the cell sap inlet, and a buffer solution passing through the buffer solution inlet jointly flow into the cell separation region 2; and the cell separation region 2 is capable of separating the inflowed cell as per a size.

The cell separation region is composed of a DLD triangular micropost array structure. From an inlet side to an outlet side, the cell separation region has a gradually increased critical sorting diameter or an unchanged critical sorting diameter. The gradually increased critical sorting diameter has a gradient from 8 μm on the inlet side (the gradient is provided every 4 μm) to 20 μm on the outlet side (a gradually increased inclination angle of a corresponding DLD microcolumn array from the inlet side to the outlet side is increased from 1.2° on the inlet side to 10.2° on the outlet side in a gradient manner, and the gradient is provided every 3°), and the unchanged critical sorting diameter is 15 μm.

The integrated chip provided by this embodiment can capture the separated target cells in situ, and directly carry out flow cytometry, sound focusing, nuleic acid or protein analysis, gene sequencing, nuleic acid library construction and cell culture analysis; or analyze with microscopy, including immunofluorescent staining and FISH staining.

The integrated chip in this embodiment is made of one or more of glass, silicon and a polymer; and the polymer is one or more of polymethyl methacrylate, polycarbonate, polystyrene, polyethylene, silicon resin (such as poly(dimethylsiloxane)), polyvinyl acetate, polypropylene, polyvinyl chloride, polyether ether ketone, a polyethylene glycol terephthalate cycloolefin polymer (COP) and a cycloolefin copolymer (COC).

Embodiment 2

Figure 2:
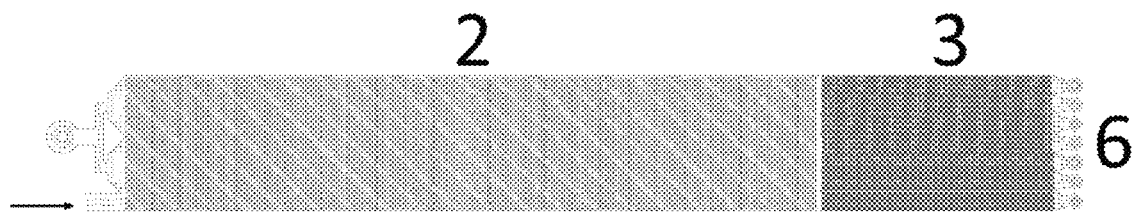
FIG. 2 is an overall structural schematic diagram of an integrated chip for separating and capturing cells with one step in Embodiment 2 of the present disclosure.

As shown in FIG. 2, an integrated chip for separating and capturing cells with one step includes a cell separation region 2 and a cell capture region 3; one end of the cell separation region 2 is provided with a cell solution inlet and a buffer solution inlet, and the other end of the cell separation region 2 is provided with an outlet; one end of the cell capture region 3 is provided with an inlet connecting with the outlet of the cell separation region 2, and the other end of the cell capture region 3 is provided with a separated liquid outlet 6; a to-be-separated cell solution passing through the cell sap inlet, and a buffer solution passing through the buffer solution inlet jointly flow into the cell separation region 2; the cell separation region 2 is capable of separating the inflowed cell as per a size; the cell separated as per the size enters the cell capture region 3; and the cell capture region 3 can capture a target cell.

The cell separation region is composed of a DLD triangular micropost array structure. From an inlet side to an outlet side, the cell separation region has a gradually increased critical sorting diameter or an unchanged critical sorting diameter. The gradually increased critical sorting diameter has a gradient from 8 μm on the inlet side (the gradient is provided every 4 μm) to 20 μm on the outlet side (a gradually increased inclination angle of a corresponding DLD micropost array from the inlet side to the outlet side is increased from 1.2° on the inlet side to 10.2° on the outlet side in a gradient manner, and the gradient is provided every 3°), and the unchanged critical sorting diameter is 15 μm.

The cell capture region includes two first regions and one second region; each first region is composed of a microcolumn capture structure array, and configured to capture the target cell; a micropost capture structure is a micropost having a large opening (having a diameter of greater than 16 μm) and a small outlet (having a diameter of 4 μm); the micropost capture structure in the microcolumn capture structure array is staggered; the second region is composed of a non-micropost capture structure array; a non-target cell flows out via the second region; a non-microcolumn capture structure is one of a triangular microcolumn, a circular microcolumn, a rectangular microcolumn, an "H-shaped microcolumn or a special-shaped structural micropost; and the non-micropost capture structure in the non-micropost capture structure array is aligned in a row.

The integrated chip provided by this embodiment can capture the separated target cells in situ, and directly carry out flow cytometry, sound focusing, nuleic acid or protein analysis, gene sequencing, nuleic acid library construction and cell culture analysis; or analyze with microscopy, including immunofluorescent staining and FISH staining.

The integrated chip in this embodiment is made of one or more of glass, silicon and a polymer; and the polymer is one or more of polymethyl methacrylate, polycarbonate, polystyrene, polyethylene, silicon resin (such as poly(dimethylsiloxane)), polyvinyl acetate, polypropylene, polyvinyl chloride, polyether ether ketone, a polyethylene glycol terephthalate cycloolefin polymer (COP) and a cycloolefin copolymer (COC).

Embodiment 3

Figure 3:
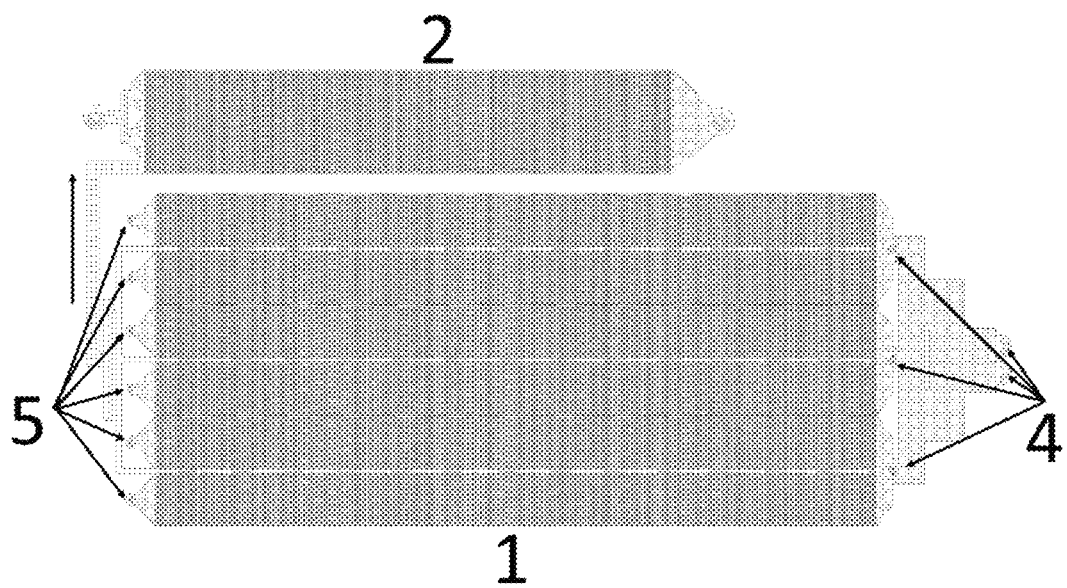
FIG. 3 is an overall structural schematic diagram of an integrated chip for separating and capturing cells with one step in Embodiment 3 of the present disclosure.

As shown in FIG. 3, an integrated chip for separating cells with one step includes a cell enrichment region 1 and a cell separation region 2; one end of the cell enrichment region 1 is provided with one or more inlets 4 to serve as a cell solution inlet and a buffer solution inlet, and the other end of the cell enrichment region 1 is provided with a waste liquid outlet 5 and an enriched liquid outlet; one end of the cell separation region 2 is provided with the buffer solution inlet and the enriched liquid inlet connecting with the enriched liquid outlet of the cell enrichment region 1, and the other end of the cell separation region 2 is provided with an outlet; a to-be-separated cell sap is perfused from the inlet of the cell enrichment region 1 to enter the cell enrichment region 1; the cell enrichment region 1 is capable of improving a concentration of target cells in the cell solution, so as to facilitate subsequent further separation; an enriched liquid flowing out from the cell enrichment region 1 and passing through the enriched liquid inlet, and a buffer solution passing through the buffer solution inlet jointly flow into the cell separation region 2; and the cell separation region 2 is capable of separating the inflowed cell as per a size.

The cell enrichment region is composed of one, two or more sets (three sets) of symmetrical DLD micropost array structures. A DLD micropost in the cell enrichment region converges to an axis of symmetry of the symmetrical DLD micropost array structure as per an inclination angle of 1.2°. Each set of DLD micropost array is separated by a column. The DLD micropost is of a triangular structure, a vertex of the triangle points to a center of the structure, an edge of the triangle is 20 µm long specifically, and a gap between two adjacent triangles is 25 µm (row space) and 50 µm (column space) specifically. The critical sorting diameter of the cell enrichment region is 6-8 µm.

The cell enrichment region is provided with one enriched liquid collection channel The enriched liquid contains a target cell and a non-target cells, and needs to be further separated.

The cell separation region is composed of the DLD triangular micropost array structure and has a gradually increased critical sorting diameter. The gradually increased critical sorting diameter has a gradient from 8 µm on the inlet side (the gradient is provided every 4 µm) to 20 µm on the outlet side (a gradually increased inclination angle of a corresponding DLD micropost array from the inlet side to the outlet side is increased from 1.2° on the inlet side to 10.2° on the outlet side in a gradient manner, and the gradient is provided every 3°).

A sample separated by the integrated chip in this embodiment may directly use one or more types of analysis in flow cytometry, sound focusing, nuleic acid or protein analysis, gene sequencing, nuleic acid library construction and cell culture. The integrated chip in this embodiment is made of one or more of glass, silicon and a polymer; and the polymer is one or more of polymethyl methacrylate, polycarbonate, polystyrene, polyethylene, silicon resin (such as poly(dimethylsiloxane)), polyvinyl acetate, polypropylene, polyvinyl chloride, polyether ether ketone, a polyethylene glycol terephthalate cycloolefin polymer (COP) and a cycloolefin copolymer (COC).

Embodiment 4

Figure 4:
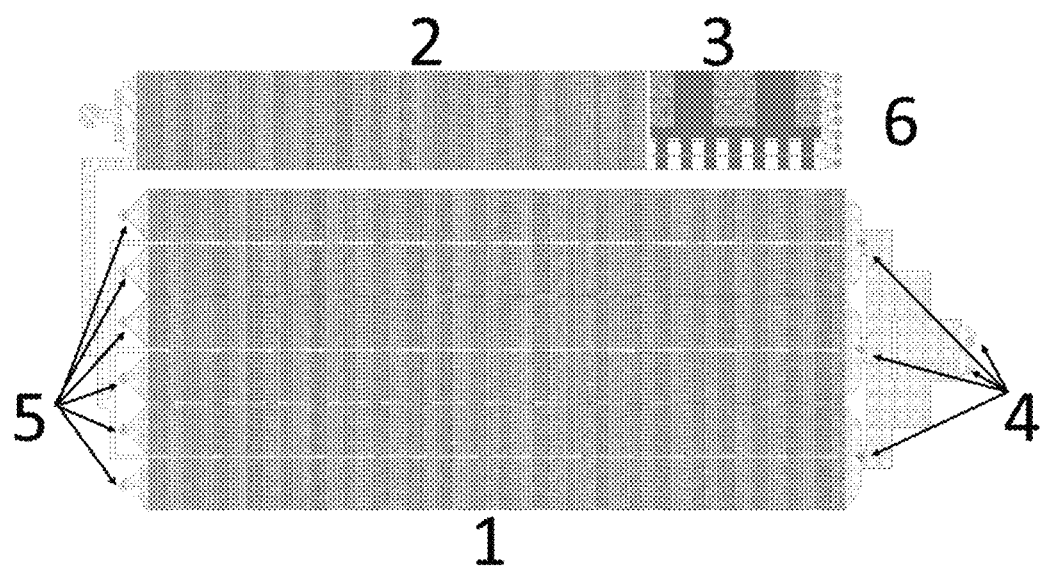
FIG. 4 is an overall structural schematic diagram of an integrated chip for separating and capturing cells with one step in Embodiment 4 of the present disclosure.
Figure 5:
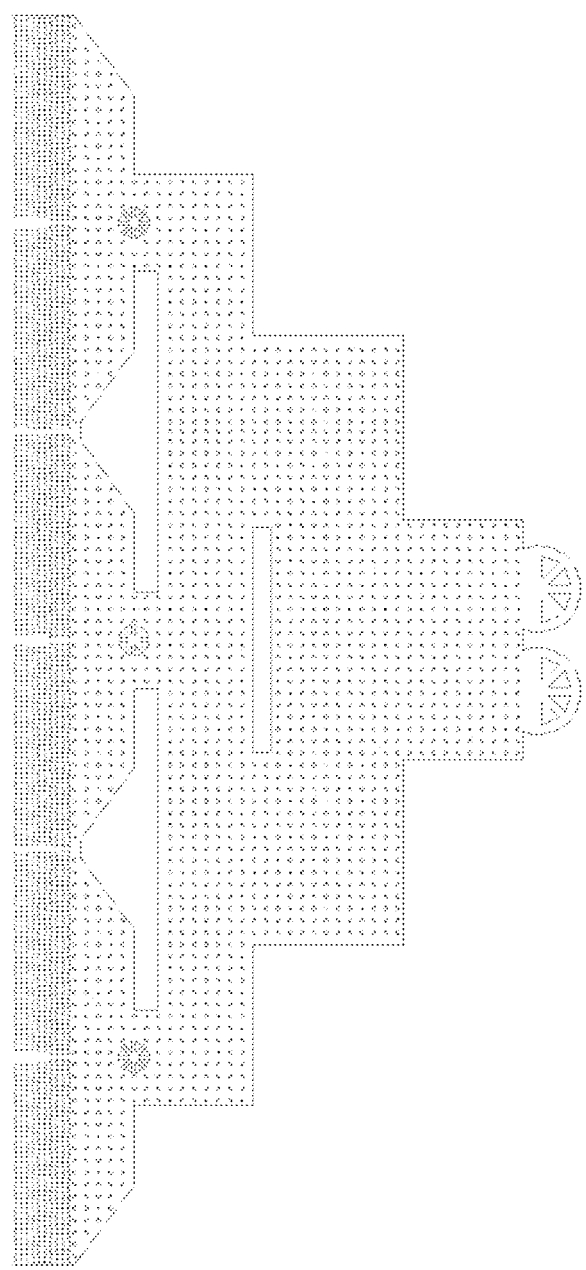
FIG. 5 is a structural schematic diagram of a to-be-separated cell solution inlet.

As shown in FIG. 4, an integrated chip for separating and capturing a cell with one step includes a cell enrichment region 1, a cell separation region 2 and a cell capture region 3; one end of the cell enrichment region 1 is provided with one or more inlets 4 (as shown in FIG. 5) to serve as a cell solution inlet and a buffer solution inlet, and the other end of the cell enrichment region 1 is provided with a waste liquid outlet 5 and an enriched liquid outlet; one end of the cell separation region 2 is provided with the buffer solution inlet and an enriched liquid inlet connecting with the enriched liquid outlet of the cell enrichment region 1, and the other end of the cell separation region 2 is provided with an outlet; one end of the cell capture region 3 is provided with an inlet connecting with the outlet of the cell separation region 2, and the other end of the cell capture region 3 is provided with a separated liquid outlet 6; a to-be-separated cell sap flows from the inlet of the cell enrichment region 1 to enter the cell enrichment region 1; the cell enrichment region 1 is capable of improving a concentration of a target cell in the cell sap, so as to facilitate subsequent further separation; a waste liquid flows out from the waste liquid outlet; an enriched liquid flowing out from the cell enrichment region 1 and passing through the enriched liquid inlet, and a buffer solution passing through the buffer solution inlet jointly flow into the cell separation region 2; the cell separation region 2 is capable of separating the inflowed cell as per a size; the cell separated as per the size enters the cell capture region 3; and the cell capture region 3 is capable of capturing the target cell.

Figure 6:
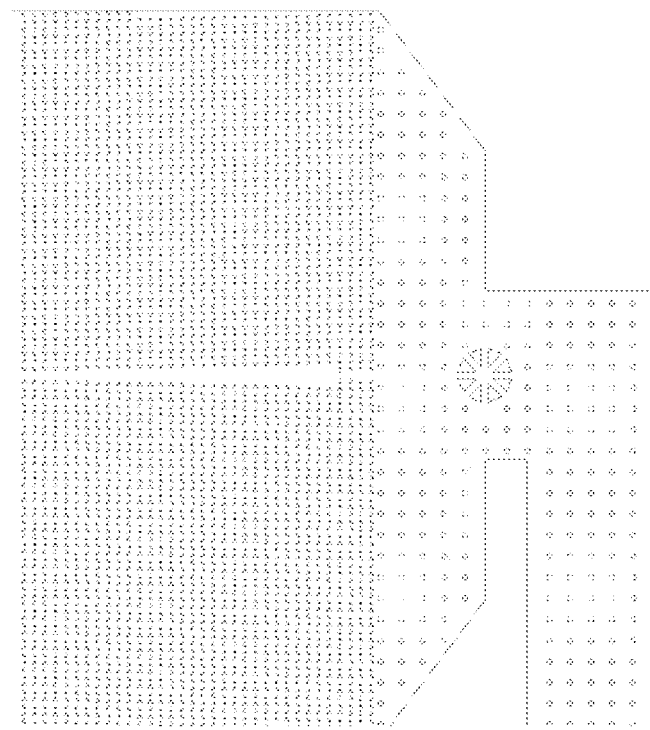
FIG. 6 is a schematic diagram of a set of symmetrical DLD micropost structure of a to-be-separated cell solution inlet side.
Figure 7:
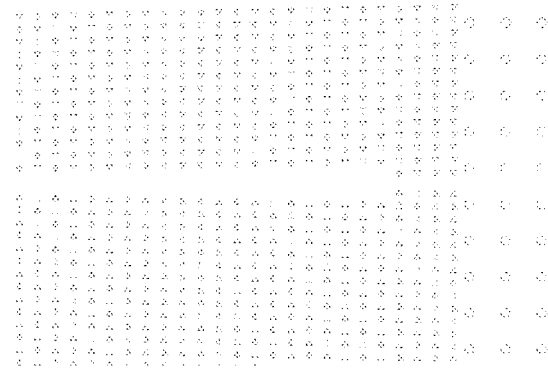
FIG. 7 is a schematic diagram of a symmetrical triangular micropost array.
Figure 8:
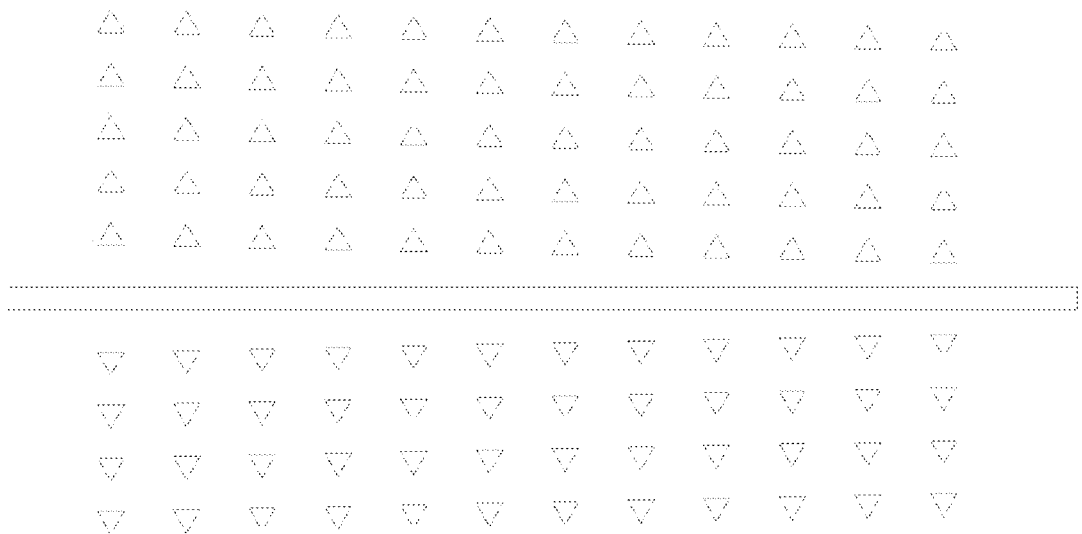
FIG. 8 is a schematic diagram of a boundary between two sets of symmetrical micropost arrays.
Figure 9:
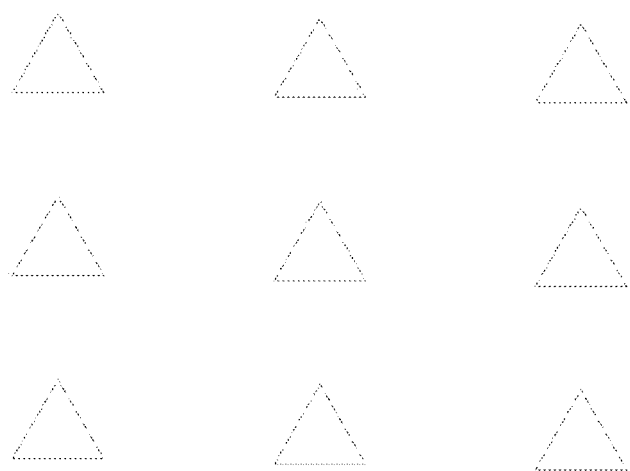
FIG. 9 is a schematic diagram illustrating a triangular micropost array structure and a size.

As shown in FIG. 5, the cell enrichment region is composed of three sets of symmetrical DLD microcolumn array structures (as shown in FIG. 6). A DLD micropost in the cell enrichment region converges to an axis of symmetry of the symmetrical DLD micropost array structure as per an inclination angle of 1.2° (as shown in FIG. 7). Each set of DLD microcolumn array is separated by a column (as shown in FIG. 8). The DLD micropost is of a triangular structure, a vertex of the triangle points to a center of the structure, an edge of the triangle is 20 µm long specifically, and a gap between two adjacent triangles is 25 µm (row space) and 50 µm (micropost gap) specifically (as shown in FIG. 9).

The critical sorting diameter of the cell enrichment region is 6-8 µm. The cell greater than the critical sorting diameter is enriched to a middle of the symmetrical DLD micropost array structure, gathers and then flows into the cell separation region. The waste liquid flows out from the waste liquid outlet.

Figure 10:
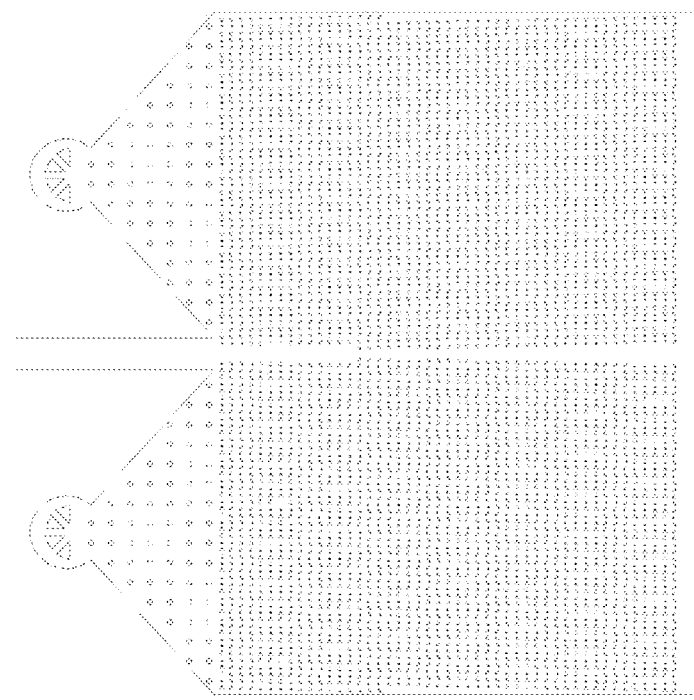
FIG. 10 is a structural schematic diagram of an outlet of an enrichment region.
Figure 11:
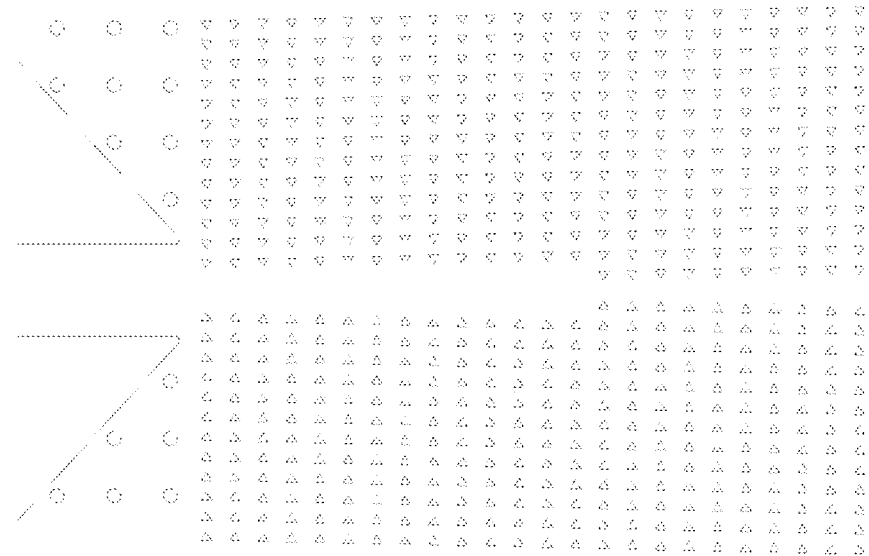
FIG. 11 is a schematic diagram of an enriched liquid collection structure.
Figure 12:
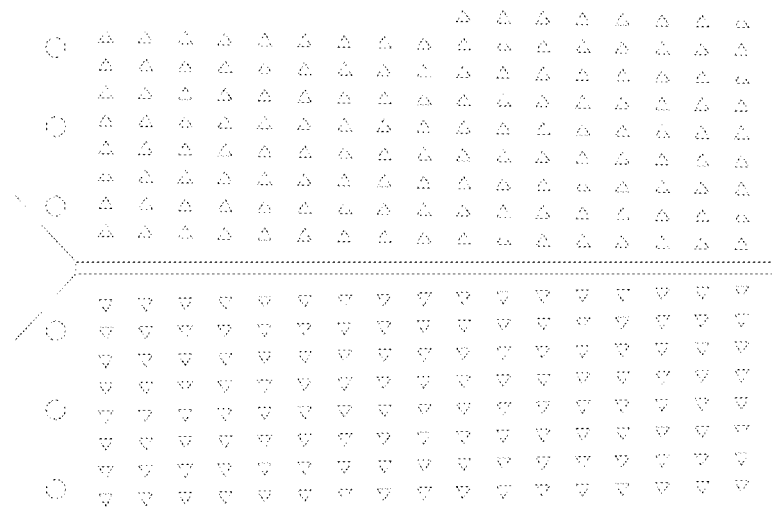
FIG. 12 is a structure of an adjacent outlet set of an enrichment region.

The cell enrichment region is provided with three enriched liquid collection channels (as shown in FIG. 10, FIG. 11 and FIG. 12). The enriched liquid contains a target cells and a non-target cells, and needs to be further separated.

The cell separation region is composed of the DLD triangular micropost array structure and has a gradually increased critical sorting diameter. The critical sorting diameter from an inlet side to an outlet side is 8-20 µm.

The gradually increased critical sorting diameter of the DLD micropost array of the cell separation region from the inlet side to the outlet side of the cell separation region is set as follows: the critical sorting diameter has a gradient from 8 µm on the inlet side (the gradient is provided every 4 µm)

to 20 μm on the outlet side (a gradually increased inclination angle of a corresponding DLD micropost array from the inlet side to the outlet side is increased from 1.2° on the inlet side to 10.2° on the outlet side in a gradient manner, and the gradient is provided every 3°).

Figure 13:
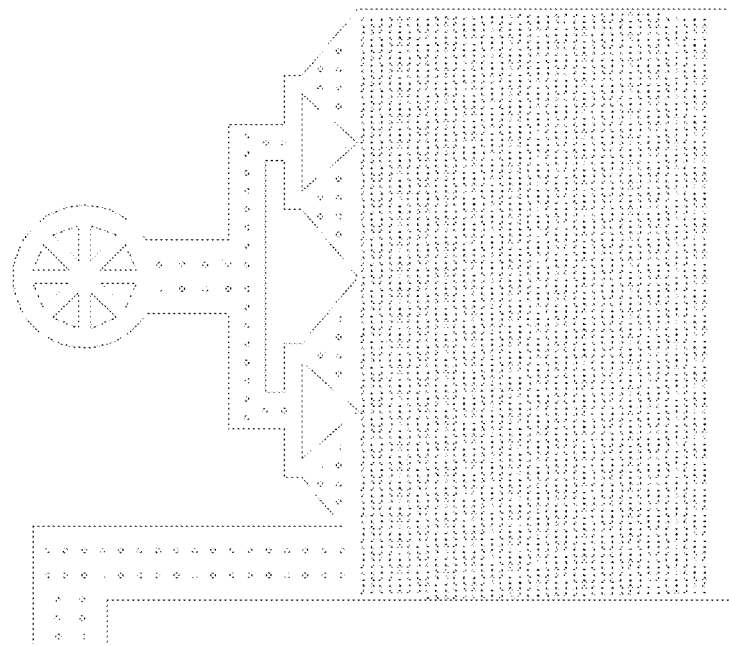
FIG. 13 is a structural schematic diagram of an inlet of a cell separation region.
Figure 14:
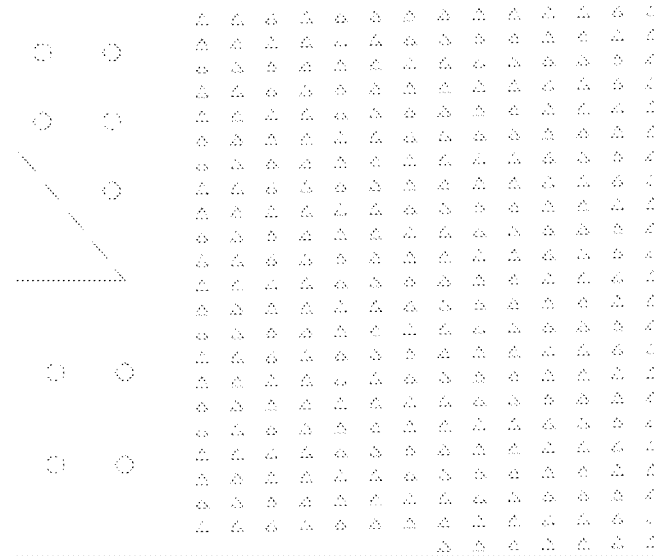
FIG. 14 is a structural schematic diagram of a separated liquid inlet of a cell separation region.
Figure 15:
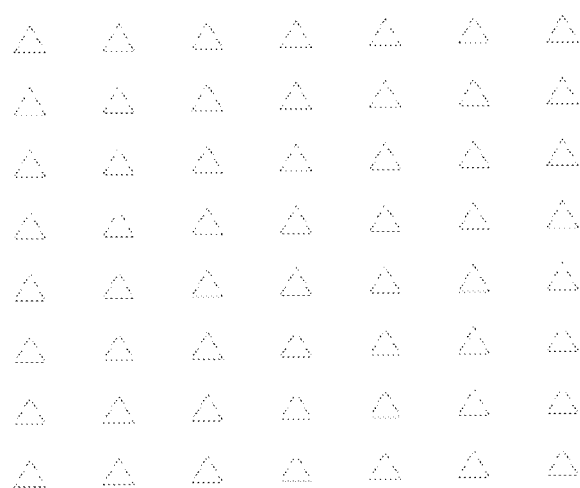
FIG. 15 is a schematic diagram of a triangular micropost array structure of a cell separation region.

The enriched liquid continues to flow through the DLD micropost array structure (as shown in FIG. 15) after the entry to the cell separation region (as shown in FIG. 13 and FIG. 14). The DLD micropost array of the cell separation region has a gradually increased inclination angle from the inlet side to the outlet side, and the inclination angle is gradually increased from 1.2° on the inlet side to 10.2° on the outlet side. A larger angle generates a larger critical separation diameter, so that the cell is spatially arranged as per the size at the outlet of the separation region.

Figure 16:
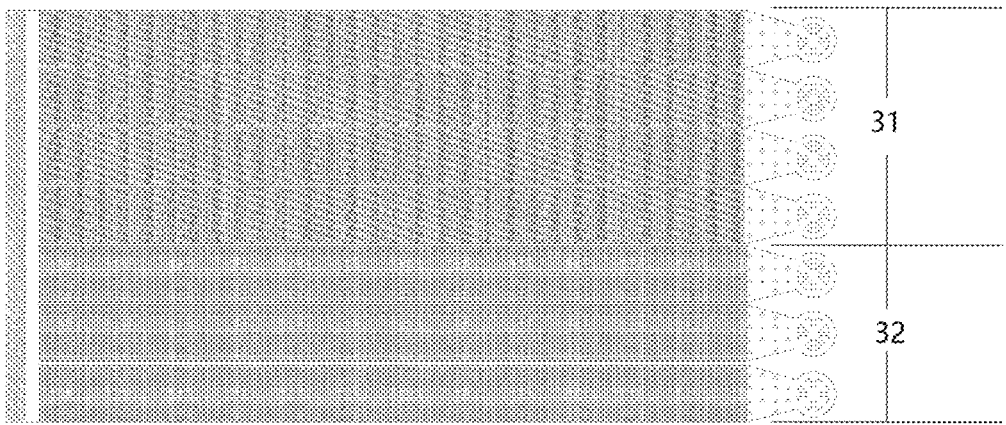
FIG. 16 is a structural schematic diagram of a cell capture region.
Figure 17:
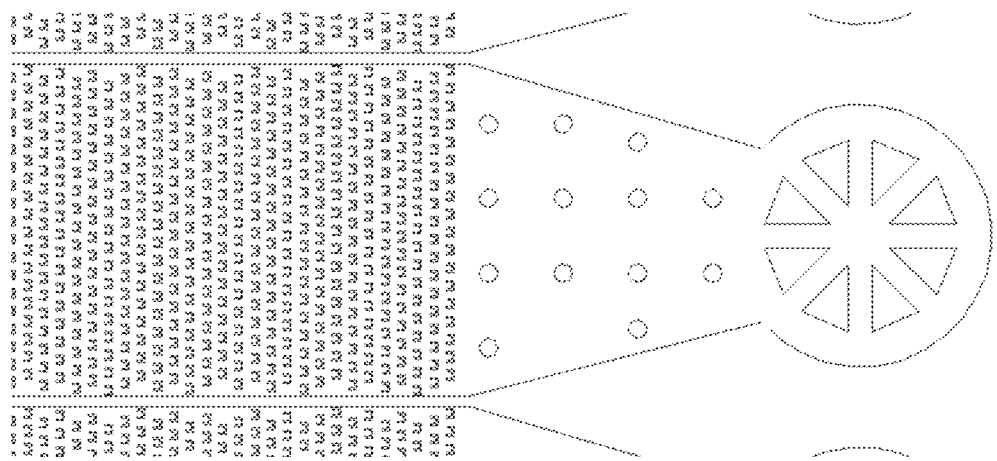
FIG. 17 is a structural schematic diagram of a first region in a cell capture region in Embodiment 4.
Figure 18:
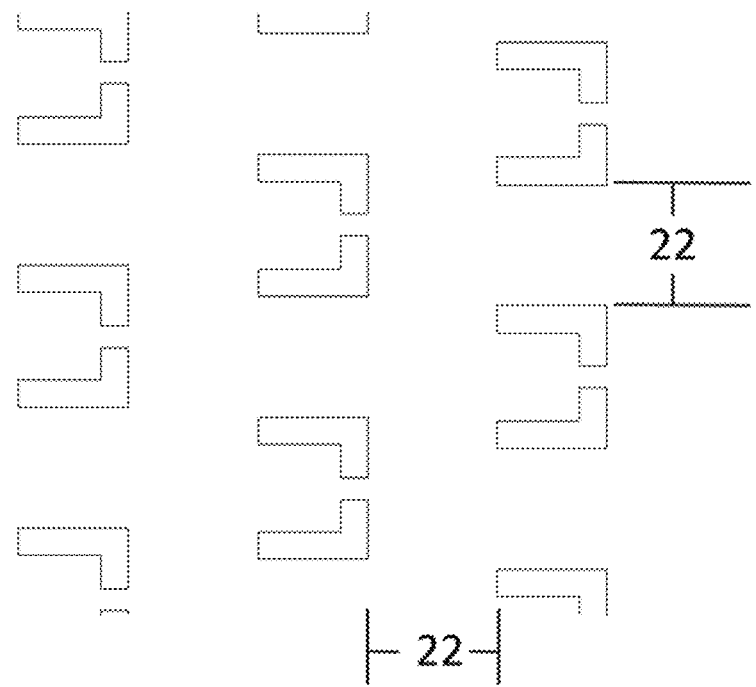
FIG. 18 is a schematic diagram of a micropost array structure of a first region in a cell capture region in Embodiment 4.
Figure 19:
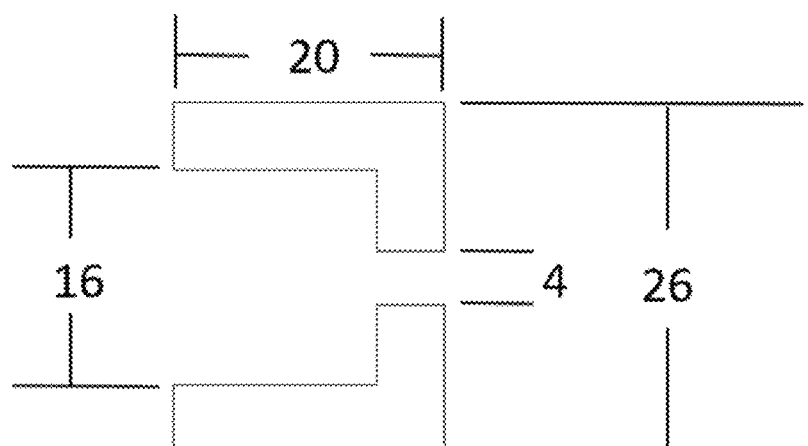
FIG. 19 is a schematic diagram of a micropost structure of a first region in a cell capture region in Embodiment 4.
Figure 20:
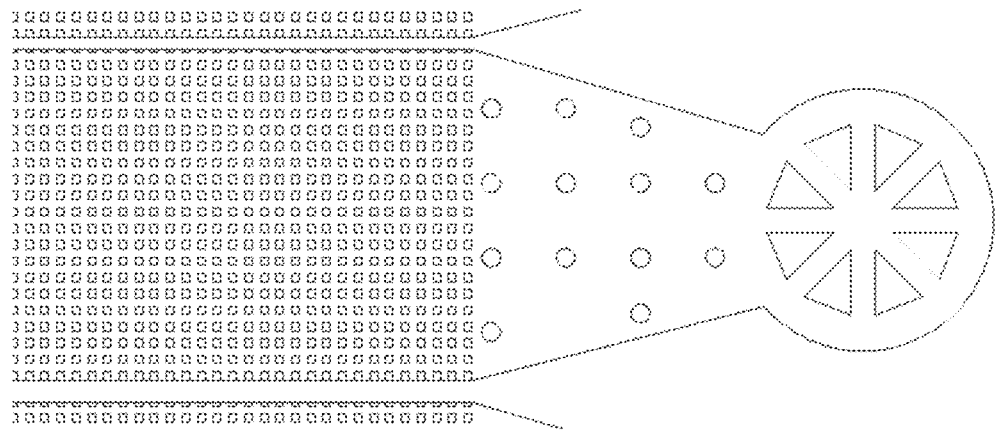
FIG. 20 is a structural schematic diagram of a second region in a cell capture region in Embodiment 4.
Figure 21:
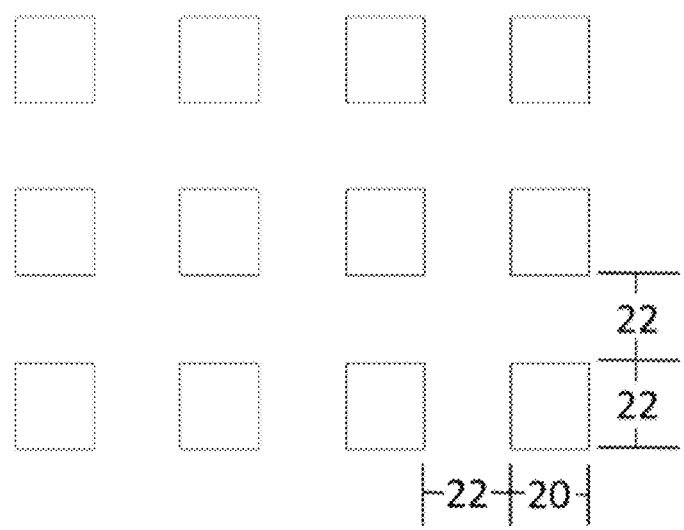
FIG. 21 is a schematic diagram of a micropost array structure of a second region in a cell capture region in Embodiment 4.

The cell spatially distributed as per the size flows into the cell capture region (as shown in FIG. 16). There are seven cell capture regions. Four first regions 31 (as shown in FIG. 17) composed of a micropost capture structure are provided and configured to capture the target cells. The micropost capture structure is a micropost having a large opening (16 μm) and a small outlet (4 μm). A vertical gap between every two adjacent microcolumn capture structures is 22 μm (as shown in FIG. 18 and FIG. 19). A non-target cell passes through a second region 32 (three second regions are provided in the capture region) composed of a rectangular non-micropost capture structure (two edges of the rectangle are 20 μm and 22 μm long respectively, and a vertical gap between every two adjacent non-micropost capture structures is 22 pm, as shown in FIG. 20), and flows out via the outlet.

The non-micropost capture structure may also be one of a triangular micropost, a circular micropost, an H-shaped micropost or a special-shaped structural micropost.

The integrated chip provided by this embodiment can capture the separated target cells in situ, and directly carry out flow cytometry, sound focusing, nuleic acid or protein analysis, gene sequencing, nuleic acid library construction and cell culture analysis; or analyze with microscopy, including immunofluorescent staining and FISH staining.

The integrated chip in this embodiment is made of one or more of glass, silicon and a polymer; and the polymer is one or more of polymethyl methacrylate, polycarbonate, polystyrene, polyethylene, silicon resin (such as poly(dimethylsiloxane)), polyvinyl acetate, polypropylene, polyvinyl chloride, polyether ether ketone, a polyethylene glycol terephthalate cycloolefin polymer (COP) and a cycloolefin copolymer (COC).

Embodiment 5

A use method of the integrated chip for separating and capturing the cell with one step includes the following steps.

A to-be-separated cell solution is perfused from an inlet of a cell enrichment region of the integrated chip provided by the present disclosure to enter the cell enrichment region, and subjected to treatment of a symmetrical DLD micropost array structure of the cell enrichment region, where the cells greater than a critical sorting diameter are enriched to a middle of the DLD micropost array structure to improve a concentration of the cells in the cell solution, gathers and then flows into the cell separation region, and a waste liquid flows out from a waste liquid outlet; an enriched liquid and a buffer solution flowing out from the cell enrichment region (a volume ratio of the enriched liquid to the buffer solution is 1:(1-50)) jointly flow into the cell separation region, and sorted by the DLD micropost array structure of the cell separation region having a gradually increased critical sorting diameter or an unchanged critical sorting diameter, where the cell in the enriched liquid is separated as per a size; the cell separated as per the size enters to a cell capture region, where a first region of a microcolumn capture structure having a large opening and a small outlet in the cell capture region captures target cells; non-target cells flow out through a second region, and a separated liquid flows out from a separated liquid outlet at last; and staining analysis and/or sequencing research is directly carried out on the cell captured in the cell capture region.

The integrated chip for separating and capturing the cell with one step in Embodiments 1-4 is used for, including but not limited to, separation and capture of any one of the followings: CTCs in a peripheral blood sample; tumor cells in a pleural effusion, peritoneal effusion, lymph fluid, urine or bone marrow sample; nucleated erythrocytes in a peripheral blood or umbilical cord blood sample; circulating endothelial cells in the peripheral blood sample; leukocytes, T cells, B cells, lymphocytes, monocytes, natural killer cells, dendritic cells, macrophages or a hematopoietic stem cells in a peripheral blood, umbilical cord blood, pleural effusion, peritoneal effusion, urine, cerebrospinal fluid or bone marrow sample; erythrocytes or a platelets in a peripheral blood, umbilical cord blood, pleural effusion, peritoneal effusion, urine or bone marrow sample; bacterium or virus in a peripheral blood, pleural effusion, peritoneal effusion, urine, saliva, plasma, serum, cerebrospinal fluid, seminal fluid, prostatic fluid or vaginal secretion sample; and an application in sperm sorting in a seminal fluid sample.

A to-be-separated sample perfused to the inlet of the enrichment region is a stoste, a diluent or a buffer solution of the to-be-separated cell solution.

Test Example

An integrated chip in Embodiment 4 and a method in Embodiment 5 (a volume ratio of an enriched liquid and a buffer solution flowing into a cell separation region is 1:10) are used to sort a hepatoma cell HepG2.

Test example 1: a total of 5 groups were experimented, each experimented for 3 times; a simulated sample in each experiment was about 10 ml of blood (that was, a non-target cell was a leukocyte and an erythrocyte in blood mainly), and the hepatoma cell HepG2 serving as a target cell was directly added to the blood; a concentration of a cancer cell was about 100 cancer cells for each milliliter; and fluxes of the five groups of experiments were respectively 5 mL/h, 10 mL/h, 15 mL/h, 20 mL/h and 25 mL/h. With sorting by the chip in Embodiment 4, an amount of a captured cell in a cell capture region was observed and calculated to analyze a capture efficiency; and three results in each group were taken and averaged, with the capture efficiency shown in FIG. 22.

Test example 2: an experiment was carried out for 3 times; a simulated sample in each experiment was about 10 ml of blood (that was, a non-target cell was a leukocyte and an erythrocyte in blood mainly), and the hepatoma cell HepG2 serving as a target cell was directly added to the blood; a concentration of a cancer cell was about 100 cancer cells for each milliliter; and a flux of the experiment was 20 mL/h. With sorting by the chip in Embodiment 4, captured cancer cells and hemocytes were observed and distinguished, and a capture purity was calculated; and three results in each group were taken and averaged, with the capture efficiency shown in FIG. 23.

Test example 3: a total of 5 groups were experimented, each experimented for 3 times; a simulated sample in each experiment was about 10 ml of blood (that was, a non-target cell was a leukocyte and an erythrocyte in blood mainly), and the hepatoma cell HepG2 serving as a target cell was directly added to the blood; a concentration of a cancer cell was about 100 cancer cells for each milliliter; and fluxes of the five groups of experiments were respectively 5 mL/h, 10 mL/h, 15 mL/h, 20 mL/h and 25 mL/h. With sorting by the chip in Embodiment 4 and activity staining analysis, a result on an activity of a captured cell was obtained; and three results in each group were taken and averaged, with the activity of the captured cell shown in FIG. 24.

Figure 22:
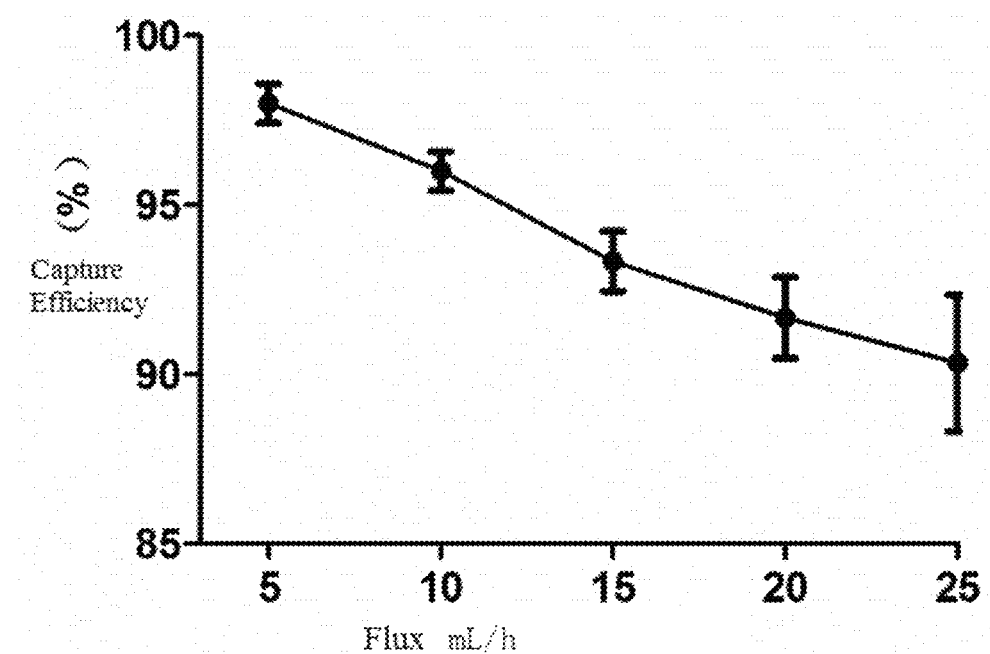
FIG. 22 is a capture efficiency of a hepatoma cell HepG2.

It may be seen from FIG. 22 that the capture efficiency of the integrated chip of the present disclosure is decreased along with an increase of the flux of the cell solution; when the flux of the cell solution is 5 mL/h, the capture efficiency reaches to 98% or more; and when the flux of the cell solution is 20 mL/h, the capture efficiency still reaches to 90% or more.

Figure 23:
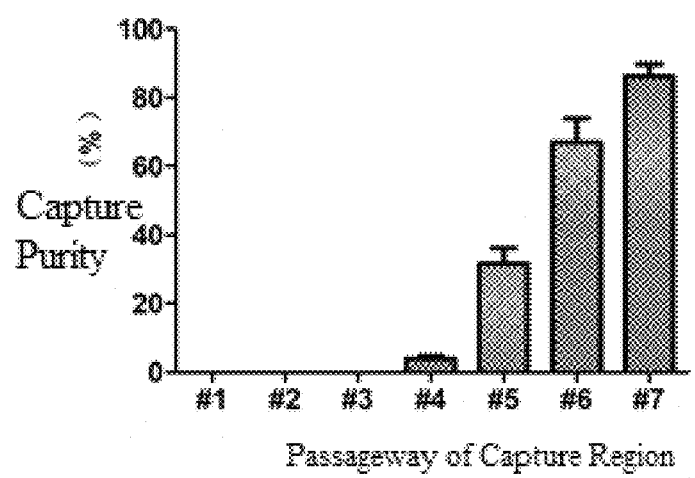
FIG. 23 is a capture purity of a hepatoma cell HepG2.

It may be seen from FIG. 23 that in the cell capture region, the capture region with a larger cell size has a higher purity of the cancer cell.

Figure 24:
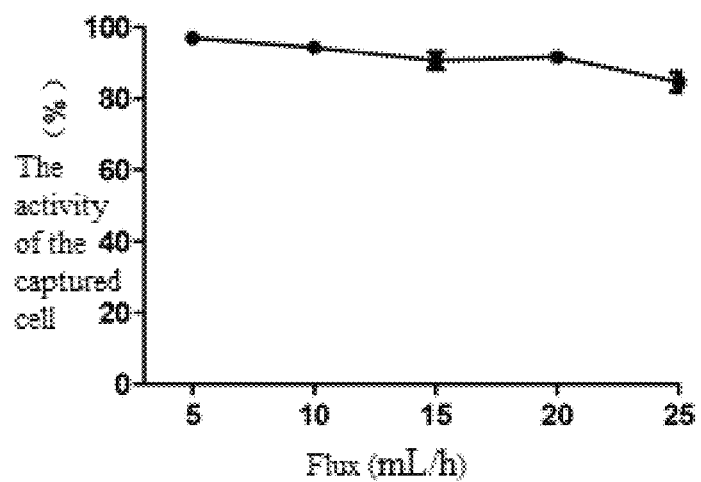
FIG. 24 is a capture activity of a hepatoma cell HepG2.

It may be seen from FIG. 24 that with the integrated chip of the present disclosure, the activity of the captured cell of the hepatoma cell HepG2 is high; when the flux of the cell sap is 5 mL/h, the activity of the separated hepatoma cell HepG2 reaches to 98%; when the flux of the cell sap is 5-20 mL/h, the activity of the separated hepatoma cell HepG2 is stable; and when the flux of the cell sap is 25 mL/h, the activity of the separated hepatoma cell HepG2 still reaches to 83%.

The above detailed description is a specific description for one of feasible embodiments of the present disclosure. This embodiment is not intended to limit a patent scope of the present disclosure. Any equivalent implementation or alteration without departing from the scope of the present disclosure should be included in the scope of the technical solution of the present disclosure.

What is claimed is:

1. An integrated chip for separating a cell with one step, comprising a cell enrichment region and a cell separation region, wherein one end of the cell enrichment region is provided with one or more inlets, and the other end of the cell enrichment region is provided with a waste liquid outlet and an enriched liquid outlet;
    one end of the cell separation region is provided with a buffer solution inlet and an enriched liquid inlet connecting with the enriched liquid outlet of the cell enrichment region, and the other end of the cell separation region is provided with an outlet;
    the cell enrichment region is composed of one, two or more sets of symmetrical Deterministic Lateral Displacement micropost array structures;
    the cell greater than a critical sorting diameter of the symmetrical DLD micropost array structure is enriched to a middle of the symmetrical DLD micropost array structure when flowing through the cell enrichment region, gathers and then flows into the cell separation region; and a waste liquid flows out from the waste liquid outlet, and a to-be-separated cell sap solution flows from the inlet of the cell enrichment region to enter the cell enrichment region;
    the cell enrichment region configured to improve a concentration of a target cell in the cell sap solution;
    an enriched liquid flowing out from the cell enrichment region and passing through the enriched liquid inlet, and a buffer solution passing through the buffer solution inlet jointly flow into the cell separation region; and the cell separation region is capable of separating the inflowed cell as per a size.

2. An integrated chip for separating and capturing a cell with one step, comprising a cell enrichment region, a cell separation region and a cell capture region, wherein one end of the cell enrichment region is provided with one or more inlets, and the other end of the cell enrichment region is provided with a waste liquid outlet and an enriched liquid outlet;
    the cell enrichment region is composed of one, two or more sets of symmetrical Deterministic Lateral Displacement micropost array structures;
    the cell greater than a critical sorting diameter of the symmetrical DLD micropost array structure is enriched to a middle of the symmetrical DLD micropost array structure when flowing through the cell enrichment region, gathers and then flows into the cell separation region; and a waste liquid flows out from the waste liquid outlet;
    one end of the cell separation region is provided with a buffer solution inlet and an enriched liquid inlet connecting with the enriched liquid outlet of the cell enrichment region, and the other end of the cell separation region is provided with an outlet; one end of the cell capture region is provided with an inlet connecting with the outlet of the cell separation region, and the other end of the cell capture region is provided with a separated liquid outlet;
    and a to-be-separated cell sap flows from the inlet of the cell enrichment region to enter the cell enrichment region; the cell enrichment region configured to improve a concentration of a target cell in the cell sap;
    an enriched liquid flowing out from the cell enrichment region and passing through the enriched liquid inlet, and a buffer solution passing through the buffer solution inlet jointly flow into the cell separation region;
    the cell separation region is capable of separating the inflowed cell as per a size;
    the cell separated as per the size enters the cell capture region; and the cell capture region is capable of capturing the target cell.

3. The integrated chip according to claim 1, wherein multiple inlets provided on one end of the cell enrichment region comprises a cell solution inlet and/or the buffer solution inlet.

4. The integrated chip according to claim 1,
    wherein when the cell enrichment region is composed of two and more sets of symmetrical DLD micropost array structures, two sets of adjacent symmetrical DLD micropost array structures are separated by a column; and
    a DLD microcolumn of the cell enrichment region is one of a triangular structure, a circular structure, a rectangular structure, an "H-shaped structure and a special-shaped structure.

5. The integrated chip according to claim 4, wherein in the cell enrichment region, the critical sorting diameter of the symmetrical DLD micropost array structure is 1-30 μm.

6. The integrated chip according to claim 4, wherein in the cell enrichment region, the DLD micropost in the symmetrical DLD micropost array structure converges to an axis of symmetry as per an inclination angle of 0.1-30° ; and
    the DLD micropost of the cell enrichment region is the triangular structure, one vertex of the triangle points to the axis of symmetry of the symmetrical DLD micropost array structure where the vertex is located, an edge of the triangle is 1-500 μm long, and a gap between two adjacent triangles is 1-500 μm.

7. The integrated chip according to claim 1, wherein the cell separation region is composed of the DLD micropost array structure;
- a DLD micropost of the cell separation region is one of a triangular structure, a circular structure, a rectangular structure, an "H-shaped structure and a special-shaped structure;
- the DLD micropost array structure of the cell separation region has a gradually increased critical sorting diameter or an unchanged critical sorting diameter from an inlet side to an outlet side of the cell separation region; and
- the gradually increased critical sorting diameter is 1-50 μm from the inlet side to the outlet side of the cell separation region; and the unchanged critical sorting diameter is 1-50 μm.

8. The integrated chip according to claim 7, wherein the DLD micropost array structure of the cell separation region has a gradually increased inclination angle from the inlet side to the outlet side of the cell separation region: the inclination angle is gradually increased from 0.1-15° on the inlet side to 0.2-30° on the outlet side.

9. The integrated chip according to claim 2, wherein the cell capture region comprises a first region and a second region;
- the first region is composed of a microcolumn capture structure array, and configured to capture the target cell; a micropost capture structure is a microcolumn having a large opening and a small outlet; and the microcolumn capture structure in the micropost capture structure array is staggered; and
- the second region is composed of a non-micropost capture structure array; a non-target cell flows out via the second region; a non-micropost capture structure is one of a triangular micropost, a circular micropost, a rectangular micropost, an "H-shaped micropost or a special-shaped micropost; and the non-micropost capture structure in the non-micropost capture structure array is aligned in a row.

10. The integrated chip according to claim 9, wherein the cell capture region has one or more first regions; and the cell capture region has one or more second regions.

11. The integrated chip according to claim 9, wherein in the first region, a diameter of the opening of the micropost capture structure is 15-30 μm, and a diameter of the outlet is 3-8 μm;
- in the micropost capture structure array, a vertical space between every two adjacent micropost capture structures is 3-30 μm; and
- in the non-micropost capture structure array, a vertical gap between every two adjacent non-micropost capture structures is 3-30 μm.

12. The integrated chip according to claim 1, wherein the integrated chip is made of one or more of glass, silicon and a polymer; and the polymer is one or more of polymethyl methacrylate, polycarbonate, polystyrene, polyethylene, silicon resin, polyvinyl acetate, polypropylene, polyvinyl chloride, polyether ether ketone, a polyethylene glycol terephthalate cycloolefin polymer and a cycloolefin copolymer.

13. A method for separating and/or capturing a cell with one step, which uses the integrated chip according to claim 2 to separate and/or capture the cell from a to-be-separated cell solution with one step, and comprises the following step: flowing the to-be-separated cell solution through a cell separation region of the integrated chip.

14. The method according to claim 13, wherein the method uses the integrated chip to separate and/or capture the cell from the to-be-separated cell solution with one step, and comprises the following steps: flowing the to-be-separated cell solution from an inlet of a cell enrichment region of the integrated chip to enter the cell enrichment region, and subjecting to treatment of a symmetrical Deterministic Lateral Displacement (DLD) micropost array structure, wherein the cell greater than a critical sorting diameter is enriched to a middle of the symmetrical DLD micropost array structure, gathers and flows into the cell separation region, and a waste liquid flows out from a waste liquid outlet; passing an enriched liquid, flowing out from the cell enrichment region, through an enriched liquid inlet, and passing a buffer solution through a buffer solution inlet, thus jointly flowing into the cell separation region, and sorting the cell by the DLD micropost array structure of the cell separation region, wherein the cell in the enriched liquid is separated as per a size; entering the cell separated as per the size to a cell capture region, wherein a first region of the cell capture region captures a target cell; and flowing out a non-target cell through a second region, and flowing out a separated liquid from a separated liquid outlet.

15. The method according to claim 14, wherein a volume ratio of the cell solution or the enriched liquid to the buffer solution flowing into the cell separation region is 1:(1-50).

16. The method according to claim 14, wherein any one of the followings is charged to the inlet of the enrichment region:
- (a) a stoste of the to-be-separated cell solution;
- (b) a diluent of the to-be-separated cell solution;
- (c) the stoste and the buffer solution of the to-be-separated cell solution; and
- (c) the diluent and the buffer solution of the to-be-separated cell solution.

17. The method according to claim 13 wherein the separated and/or captured cell comprises:
- (1) a Circulating Tumor Cell in a peripheral blood sample;
- (2) a tumor cell in a pleural effusion, peritoneal effusion, lymph fluid, urine or bone marrow sample;
- (3) a nucleated erythrocyte in a peripheral blood or umbilical cord blood sample;
- (4) a circulating endothelial cell in the peripheral blood sample;
- (5) a leukocyte, a T cell, a B cell, a lymphocyte, a monocyte, a natural killer cell, a dendritic cell, a macrophage or a hematopoietic stem cell in a peripheral blood, umbilical cord blood, pleural effusion, peritoneal effusion, urine, cerebrospinal fluid or bone marrow sample;
- (6) an erythrocyte or a platelet in a peripheral blood, umbilical cord blood, pleural effusion, peritoneal effusion, urine or bone marrow sample;
- (7) a bacterium or a virus in a peripheral blood, pleural effusion, peritoneal effusion, urine, saliva, plasma, serum, cerebrospinal fluid, seminal fluid, prostatic fluid or vaginal secretion sample; and
- (8) a sperm in a seminal fluid sample.

18. The integrated chip according to claim 1 wherein when the cell enrichment region is composed of two and more sets of symmetrical DLD micropost array structures, two sets of adjacent symmetrical DLD micropost array structures are separated by a column; and
- a DLD micropost of the cell enrichment region is one of a triangular structure, a circular structure, a rectangular structure, an "H-shaped structure and a special-shaped structure.

19. The integrated chip according to claim 1 wherein multiple inlets provided on one end of the cell enrichment region comprises a cell solution inlet and/or the buffer solution inlet.

20. The integrated chip according to claim 1 wherein the cell separation region is composed of the DLD micropost array structure;
- a DLD micropost of the cell separation region is one of a triangular structure, a circular structure, a rectangular structure, an "H-shaped structure and a special-shaped structure;
- the DLD microcolumn array structure of the cell separation region has a gradually increased critical sorting diameter or an unchanged critical sorting diameter from an inlet side to an outlet side of the cell separation region; and
- the gradually increased critical sorting diameter is 1-50 μm from the inlet side to the outlet side of the cell separation region; and the unchanged critical sorting diameter is 1-50 μm.

* * * * *